United States Patent [19]

Takeuchi et al.

[11] Patent Number: 5,498,739
[45] Date of Patent: Mar. 12, 1996

[54] METHOD FOR INTRODUCING HYDROCARBONS INTO CHLOROSILANES

[75] Inventors: Masaki Takeuchi; Akira Yamamoto; Mikio Endo, all of Niigata, Japan

[73] Assignee: Shin-Etsu Chemical Co., Ltd., Tokyo, Japan

[21] Appl. No.: 360,020

[22] Filed: Dec. 20, 1994

[30] Foreign Application Priority Data

Dec. 21, 1993 [JP] Japan .................................. 5-345212
Feb. 15, 1994 [JP] Japan .................................. 6-040500
Jun. 7, 1994 [JP] Japan .................................. 6-148660

[51] Int. Cl.$^6$ .................................................... C07F 7/08
[52] U.S. Cl. ............................................. 556/478; 556/430
[58] Field of Search ................................. 556/478, 430

[56] References Cited

U.S. PATENT DOCUMENTS

| | | |
|---|---|---|
| 2,403,370 | 2/1945 | Hurd . |
| 4,155,927 | 5/1979 | Straussberger et al. ............... 556/478 |
| 4,400,528 | 8/1983 | Artes et al. . |
| 4,946,980 | 8/1990 | Halm et al. ............................ 556/478 |
| 5,175,331 | 12/1992 | Park et al. ............................. 556/478 |
| 5,177,235 | 1/1993 | Eisenberg et al. ..................... 556/478 |

FOREIGN PATENT DOCUMENTS

| | | |
|---|---|---|
| 365206 | 4/1990 | European Pat. Off. . |
| 405780 | 1/1991 | European Pat. Off. . |
| 505843 | 11/1982 | France . |
| 987443 | 12/1961 | United Kingdom . |
| 005707 | 4/1979 | United Kingdom . |

OTHER PUBLICATIONS

English language abstract of JP-B-61007433, Jan. 14, 1986.

*Primary Examiner*—Paul T. Shaver
*Attorney, Agent, or Firm*—Birch, Stewart, Kolasch & Birch

[57] ABSTRACT

By reacting a chloromonosilane or chlorodisilane with a halogenated hydrocarbon in a liquid phase in the presence of metallic aluminum or an aluminum alloy, a hydrocarbon group is substituted for at least one chlorine atom of the chlorosilane for introducing hydrocarbon into the chlorosilane. Silanes having a high degree of hydrocarbon substitution can be easily synthesized from chlorosilanes under moderate conditions and with high volumetric efficiency. The reagents used are aluminum or aluminum alloys and halogenated hydrocarbons which are inexpensive and readily available.

21 Claims, No Drawings

METHOD FOR INTRODUCING HYDROCARBONS INTO CHLOROSILANES

BACKGROUND OF THE INVENTION

1. Field of the Invention

This invention relates to a method for introducing a hydrocarbon into a chlorosilane under moderate conditions using inexpensive reagents.

2. Prior Art

Chlorosilanes having a high degree of alkyl substitution and derivatives thereof have found a wide variety of applications in the industry. For example, trimethylchlorosilane is not only widely used as a silylating agent, but is also effective for rendering inorganic substances hydrophobic and introducing terminal block units into organopolysiloxane chains. t-butyldimethylchlorosilane is also widely used as a silylating agent for the synthesis of intermediates of medicine. Hexamethyldisilane is also useful as a silylating agent of medicines and other products.

Since a distillation kettle for producing silanes contains methylchlorodisilanes having a high degree of chlorine substitution, it is of industrial significance to methylate the methylchlorodisilanes for conversion into disilanes having a high degree of methyl substitution.

For alkylating chloromonosilanes, Grignard reagents are conventionally used. This method has the disadvantages that metallic magnesium is expensive and a large volume of solvent must be used to detract from volumetric efficiency. In Z. Anorg. Allgem. Chem., 287273 (1956), an attempt was made to methylate chlorosilanes using methylaluminum-sesquichloride. It is known that one of the reagents, methylaluminum-sesquichloride is spontaneously ignitable in air and undergoes explosive hydrolysis in the presence of a trace amount of water. This attempt is dangerous for commercial synthesis.

Japanese Patent Application Kokai (JP-A) No. 256688/1990 discloses a method for methylating a chlorosilane by effecting a gas phase reaction between a chlorosilane and methyl chloride gas in a reactor tube at 180° to 450° C. This method is also dangerous in that the reaction requires a high temperature, and aluminum chloride as a by-product tends to clog the reactor tube.

Also known in the art are alkylation of chlorosilanes using alkyllithium and alkylsodium (see J. Am. Chem. Soc., 68, 1675 (1946)) and alkylation of chlorosilanes using alkylzinc (see Ann., 222, 354 (1884)). These methods are not commercially acceptable since they are inferior in safety and operation efficiency. Particularly the latter method is low in yield.

As mentioned above, the prior art methods for preparing monosilanes having a high degree of alkyl substitution suffer from problems including the use of expensive reagents, complex operation, and a high cost.

As to the methylation of chlorodisilanes, a method using Grignard reagents is also conventional as described in Kumada et al., J. Org. Chem., 21 (1956), 1264–1268. This conventional method has the disadvantages that metallic magnesium is expensive and a large volume of solvent must be used to detract from volumetric efficiency.

Japanese Patent Publication (JP-B) No. 7433/1986 proposes to carry out methylation reaction by effecting disproportionation between a chlorodisilane and tetramethylsilane in the presence of an organic aluminum compound such as ethyl aluminumsesquichloride, a silane compound containing a Si—H bond, and hydrogen chloride gas. This methylation, however, must use the organic aluminum compound, which is spontaneously ignitable and thus quite dangerous, and the tetramethylsilane which has a low boiling point and is thus inconvenient to store and handle. Because of thermodynamic equilibrium, it is essentially impossible to obtain disilanes having a high degree of methyl substitution in high yields. These facts, combined with complex operation and potential danger, render this method commercially unacceptable.

Among disilanes having a high degree of methyl substitution, hexamethyldisilane is of particular importance. In addition to the above-mentioned methods, it is also known in the prior art to prepare hexamethyldisilane through condensation of trimethylhalogenosilane using alkali metals. Methods using metallic lithium are disclosed, for example, in H. Gilman et al., J. Organometal. Chem., 13, 323 (1968); Sakurai et al., JP-A 42616/1974; D. E. Seilz et al., Synth. Commun., 9, 451 (1981); and G. Fritz et al., Z. Anorg. Allg. Chem., 473, 59 (1981). Methods using metallic sodium are disclosed, for example, in W. Sundermeyer et al., z. Anorg. U. Allgem. Chem., 310, 50 (1961); G. R. Wilson et al., J. Org. Chem., 26, 557 (1961); and M. G. Voronkov et al., Z. Obs. Khim., 26, 584 (1956). Since most of these methods use polar solvents such as tetrahydrofuran and hexamethylphosphoramide and commercially uncommon techniques such as ultrasonic techniques, they suffer from the problems of solvent recovery, inferior volumetric efficiency, and complex process. The use of alkali metals which are dangerous is also a problem in insuring industrial safety. It is further known to condense trimethylchlorosilane using magnesium (see L. Roesch et al., Z. Naturforsch. B: Anorg. Chem. Org. Chem., 31b, 281 (1976)). This method uses magnesium which is expensive and hexamethylphosphorotriamide which is recently regarded carcinogenic. This method is now unacceptable.

There is a desire to have a method for introducing hydrocarbons into chlorosilanes for producing silanes having a high degree of hydrocarbon substitution while avoiding economical and operational problems.

SUMMARY OF THE INVENTION

An object of the present invention is to provide a method for producing a silane having a high degree of hydrocarbon substitution by substituting an organic hydrocarbon group for a chlorine atom of a chlorosilane under moderate conditions using inexpensive reagents.

For introducing a hydrocarbon into a chlorosilane, we have attempted to react a chlorosilane with a halogenated hydrocarbon in a liquid phase in the presence of metallic aluminum or an aluminum alloy and have found that a hydrocarbon group is substituted for at least one chlorine atom of the chlorosilane. The chlorosilane is of the general formula (1) or (2):

$$R_m SiCl_{4-m} \tag{1}$$

$$R_n Si_2 Cl_{6-n} \tag{2}$$

wherein R is a hydrogen atom or monovalent hydrocarbon group, a plurality of R groups may be identical or different, letter m is an integer of 0 to 3, and n is an integer of 0 to 5. The halogenated hydrocarbon is of the general formula (3):

$$R'X \tag{3}$$

wherein R' is a monovalent hydrocarbon group and X is a halogen atom. This method enables the introduction of a hydrocarbon into a chlorosilane through a safe and simple operation under moderate conditions, using reagents which are inexpensive, readily available, safe, and easy to handle. As a result, a silane having a high degree of hydrocarbon substitution can be produced in high yields.

Particularly when a chlorosilane of the general formula (1A) or (2A):

$$R_xSiCl_{4-x} \tag{1A}$$

$$R_ySi_2Cl_{6-y} \tag{2A}$$

wherein R is as defined above, x is an integer of 0 to 2, and y is an integer of 0 to 4 is reacted with a halogenated hydrocarbon of formula (3) in the presence of a silane of the general formula (4):

$$R'_bSi_aCl_{2a+2-b} \tag{4}$$

wherein R' is as defined above, letter a is an integer of at least 1 and b is equal to 2a, 2a+1 or 2a+2, the rate of reaction of introducing a hydrocarbon into a silane having a high degree of chloro substitution can be increased. Then silanes having a high degree of hydrocarbon substitution, such as tetramethyl-silane and hexamethyldisilane can be efficiently produced.

Accordingly, the present invention provides a method for introducing a hydrocarbon into a chlorosilane by reacting a chlorosilane of formula (1) or (2) with a halogenated hydrocarbon of formula (3) in a liquid phase in the presence of metallic aluminum or an aluminum alloy, thereby substituting a hydrocarbon for at least one chlorine atom of the chlorosilane. Preferably a chlorosilane of formula (1A) or (2A) is reacted in the further presence of a silane of formula (4).

DETAILED DESCRIPTION OF THE INVENTION

The present invention pertains to the introduction of hydrocarbons into chlorosilanes. That is, the invention pertains generally to hydrocarbylation, often alkylation, typically methylation of chlorosilanes. Although alkylation is frequently used throughout the specification for convenience of description, the term "alkylation" should be interpreted in a broader sense as encompassing the introduction of hydrocarbons into chlorosilanes.

One of the starting materials is a chlorosilane which includes chloromonosilanes and chlorodisilanes of the general formula (1) and (2).

$$R_mSiCl_{4-m} \tag{1}$$

$$R_nSi_2Cl_{6-n} \tag{2}$$

In the formulae, R is a hydrogen atom or monovalent hydrocarbon group. The monovalent hydrocarbon group preferably has 1 to 20 carbon atoms, especially 1 to 6 carbon atoms and may be either saturated or unsaturated. Examples include alkyl groups such as methyl, ethyl, propyl, and butyl, and alkenyl groups such as vinyl while those hydrocarbon groups free of an aliphatic unsaturated bond are preferred. Where there is more than one R group, they may be identical or different. Letter m is an integer of 0, 1, 2 or 3. Letter n is an integer of 0 to 5, preferably an integer of 2 to 5, more preferably equal to 2 or 3.

Examples of the chloromonosilane of formula (1) include tetrachlorosilane, methyltrichlorosilane, methylhydrogendichlorosilane, dimethyldichlorosilane, dimethylhydrogenchlorosilane, ethyltrichlorosilane, and isopropyltrichlorosilane.

Examples of the chlorodisilane of formula (2) include 1,1,2,2-tetrachloro-1,2-dimethyldisilane, 1,1,1,2-tetrachloro-2,2-dimethyldisilane, 1,1,2-trichloro-1,2,2-trimethyldisilane, 1,2-dichloro-1,1,2,2-tetramethyldisilane, 1,1-dichloro-1,2,2,2-tetramethyldisilane, 1-chloro-1,1,2,2,2-pentamethyldisilane, and 1,1-dichloro-1,2,2,2-tetraethyldisilane.

The other starting material is a halogenated hydrocarbon which is used for introducing a hydrocarbon into the starting chlorosilane. The halogenated hydrocarbon is represented by the general formula (3).

$$R'X \tag{3}$$

R' is a monovalent hydrocarbon group, preferably having 1 to 10 carbon atoms, more preferably 1 to 6 carbon atoms, typically an alkyl or cycloalkyl group. X is a halogen atom such as chlorine, fluorine, bromine, and iodine, preferably chlorine. Examples of the halogenated hydrocarbon include those which are gaseous at room temperature, such as methyl chloride and ethyl chloride and those which are liquid at room temperature, such as t-butyl chloride, cyclohexyl chloride, methyl iodide, and ethyl bromide. Among the above-mentioned halogenated hydrocarbons, methyl chloride and ethyl chloride are preferred.

Desirably, the halogenated hydrocarbon is used in an amount of about 1 to 1.5 mol, especially about 1 to 1.2 mol per mol of a Si—Cl bond to be alkylated in the starting chlorosilane. If the amount of halogenated hydrocarbon used is less than 1 mol on this basis, reaction would not proceed to an acceptable extent, resulting in low reactivity. If the amount of halogenated hydrocarbon exceeds 1.5 mol, the selectivity of the desired silane would be low.

According to the present method, a chlorosilane to be alkylated is mixed by agitation with metallic aluminum or an aluminum alloy in a liquid phase, into which a halogenated hydrocarbon is admitted. The halogenated hydrocarbon may be admitted in gaseous state or added dropwise in liquid state to a chlorosilane in liquid phase having aluminum or aluminum alloy dispersed therein.

The metallic aluminum and aluminum alloy used herein preferably include Al, AlMgSi, and AlCuMg, and are in the form of particles. The aluminum alloy should preferably contain more than 85% by weight of aluminum. Even if metallic aluminum and aluminum alloys are used as such, reaction can take place to a sufficient extent. However, it is preferred to previously activate metallic aluminum and aluminum alloys since metallic aluminum and aluminum alloys are generally covered on the surface with an oxide film. Activation can be done by passing dry hydrogen chloride gas at about 60° to 150° C. or by heating a mixture of aluminum and iodine chips. Alternatively, ethyl bromide, ethylene bromide or iodine is admitted into a dispersion of metallic aluminum or aluminum alloy in a starting chlorosilane for activating aluminum.

Desirably, metallic aluminum or aluminum alloy is used in an amount of about 0.6 to 2.7 mol, especially about 0.6 to 1 mol per mol of a Si—Cl bond to be alkylated in a chlorosilane of formula (1) or (2). If the amount of aluminum used is less than 0.6 mol on this basis, chlorosilanes would be low in reactivity. If the amount of aluminum exceeds 2.7 mol, there would be left much unreacted aluminum which would require cumbersome post-treatment.

In one preferred embodiment of the invention wherein the chlorosilane is of the general formula (1A) or (2A):

$$R_xSiCl_{4-x} \quad (1A)$$

$$R_ySi_2Cl_{6-y} \quad (2A)$$

wherein R is as defined above, x is an integer of 0 to 2, and y is an integer of 0 to 4, the reaction rate can be increased by adding to the reaction system at least one silane of the general formula (4):

$$R'_bSi_aCl_{2a+2-b} \quad (4)$$

wherein R' is as defined above, letter a is an integer of at least 1, preferably 1 to 10 and b is equal to 2a, 2a+1 or 2a+2. More particularly, the silanes of formula (4) are those of formulae (4A), (4B) and (4C).

$$R'_{2a}Si_aCl_2 \quad (4A)$$

$$R'_{2a+1}Si_aCl \quad (4B)$$

$$R'_{2a+2}Si_a \quad (4C)$$

Examples of the silane of formula (4) include dichlorodimethylsilane, chlorotrimethylsilane, tetramethylsilane, 1-chloro-1,1,2,2,2-pentamethyldisilane, hexamethyldisilane, 1-chloroheptamethyltrisilane, octamethyltrisilane, decamethyltetrasilane, tetraethylsilane, hexaethyldisilane, and octaethyltrisilane, with the chlorotrimethylsilane, tetramethylsilane, hexamethyldisilane, octamethyltrisilane, and decamethyltetrasilane being preferred.

Preferred among the silanes of formula (4) are those of formula (4) wherein b=2a+2, that is, those of the general formula (4C):

$$R'_{2a+2}Si_a \quad (4C)$$

wherein a is as defined above, preferably an integer of 1, 2 or 3, more preferably 2 or 3. These preferred silanes are exemplified by tetramethylsilane, hexamethyldisilane, octamethyltrisilane, decamethyltetrasilane, tetraethylsilane, hexaethyldisilane, and octaethyltrisilane. When a silane of formula (4C) is added to the reaction system, the reaction rate is increased, enabling reaction at lower temperatures and minimizing the formation of by-products.

Desirably the silane of formula (4) is added in an amount of about 1 to 20 mol %, especially about 1 to 10 mol % based on the starting chlorosilane. Less than 1 mol % of the silane of formula (4) would be ineffective whereas more than 20 mol % would increase the internal pressure of the reaction system and trigger formation of by-products.

According to the present method, a chlorosilane to be alkylated is mixed by agitation with metallic aluminum or an aluminum alloy in a liquid phase, into which a halogenated hydrocarbon (e.g., methyl chloride) and an optional reaction accelerating silane of formula (4) are admitted, thereby effecting alkylation reaction.

In the practice of the invention, the chlorosilanes of formulae (1) and (2) are used in a liquid phase. As long as the chlorosilanes remain liquid, reaction can be effected in the absence of a solvent. If desired, an inert solvent such as n-nonane, n-decane, decalin (decahydronaphthalene) and toluene may be used.

The alkylation reaction is preferably effected at a temperature of 20° to 150° C., more preferably 50° to 100° C. and a pressure of 0 to 10 kgw/cm²G, more preferably 2 to 7 kgw/cm²G (gage pressure) for a time of about 5 to 20 hours. It is understood that the reaction time and pressure may be adjusted in accordance with the vapor pressure of starting materials and the reaction temperature.

At the end of alkylation reaction, the reaction liquid is distilled directly or after filtration for recovering an alkylated silane (broadly a silane having a hydrocarbon introduced therein). It is noted that the still residue of direct distillation or the residue of filtration consists essentially of aluminum chloride and a small amount of unreacted aluminum. The aluminum chloride may be recovered by sublimation. The unreacted aluminum may be treated with acids or alkaline water.

A second preferred embodiment of the inventive method employs two stages of reaction of first effecting redistribution reaction between a chlorosilane of formula (1) or (2) and a silane of formula (4) in the presence of a Lewis acid catalyst, then adding aluminum or aluminum alloy, and admitting a halogenated hydrocarbon (e.g., methyl chloride) into the reaction system. This embodiment is effective especially for the synthesis of highly alkylated silanes such as trimethylchlorosilane and hexamethyldisilane.

In the second embodiment, a silane of formula (4C) is preferably used as the silane of formula (4). The silane of formula (4) is desirably used in an amount of (3-x)/2 mol to 5(3-x) mol, especially (3-x) mol to 2(3-x) mol per mol of the chloromonosilane of formula (1) or in an amount of (5-y)/2 mol to 5(5-y) mol, especially (5-y) mol to 2(5-y) mol per mol of the chlorodisilane of formula (2) wherein x and y are as defined above.

The Lewis acid catalyst for promoting disproportionation between a chlorosilane of formula (1) or (2) and a silane of formula (4) includes aluminum chloride, aluminum bromide, boron trichloride, and ferric chloride, with the aluminum chloride being preferred. The amount of Lewis acid catalyst used is preferably 0.5 to 10%, more preferably 1 to 5% by weight of the chlorosilane of formula (1) or (2).

While redistribution reaction is effected between a chlorosilane of formula (1) or (2) and a silane of formula (4) in the presence of a Lewis acid catalyst in the first stage, the aluminum or aluminum alloy to be added in the second stage may be previously added to the reaction system. This reaction is preferably effected at a temperature of 20° to 150° C., more preferably 50° to 100° C. and a pressure of 0 to 10 kg/cm²G, more preferably 0 to 5 kg/cm²G (gage pressure) for a time of about ½ to 5 hours. A catalytic amount of a Si—H bond-containing silane such as methyldichlorosilane may be added for promoting the redistribution reaction. The highly alkylated silane may be once isolated from the redistribution reaction solution by distillation if desired, prior to the second stage of admitting a halogenated hydrocarbon for further reaction. The reaction with a halogenated hydrocarbon in the second stage is the same as in the preceding embodiment and the work-up process at the end of reaction is also the same as previously mentioned.

When it is desired to produce hexamethyldisilane, for example, in accordance with the second embodiment, the starting material is preferably a chlorodisilane of the following general formula (2B):

$$(CH_3)_cSi_2Cl_{6-c} \quad (2B)$$

wherein c is an integer of 0 to 4. The chlorodisilane is reacted with a stoichiometrically excess amount of a silane of formula (4C) wherein R' is methyl in the presence of a Lewis acid catalyst, obtaining a reaction solution containing pentamethylchlorodisilane as a main ingredient. Thereafter, metallic aluminum or aluminum alloy is dispersed in the reaction solution, into which methyl chloride is admitted for selectively synthesizing hexamethyldisilane.

When it is desired to produce tetra methylsilane, for example, in accordance with the second embodiment, the starting material is preferably a chlorosilane of the following general formula (1B):

$$(CH_3)_d SiCl_{4-d} \tag{1B}$$

wherein d is an integer of 0 to 2. The chlorosilane is reacted with a stoichiometrically excess amount of a silane of formula (4C) wherein R' is methyl in the presence of a Lewis acid catalyst, obtaining a reaction solution containing trimethylchlorosilane as a main ingredient. Thereafter, metallic aluminum or aluminum alloy is dispersed in the reaction solution, into which methyl chloride is admitted for selectively synthesizing tetramethylsilane.

According to the present invention, by reacting a chloromonosilane of formula (1) with a halogenated hydrocarbon of formula (3), there is obtained a hydrocarbon-containing monosilane of the general formula (5):

$$R_m R'_k SiCl_{4-m-k} \tag{5}$$

wherein R, R' and m are as defined above, k is an integer of at least 1, $m+k \leq 4$.

When a chlorodisilane of formula (2) is used, at least one chlorine atom thereof is replaced by a hydrocarbon (e.g., methyl) to provide a disilane having a high degree of hydrocarbon substitution. That is, there is obtained a disilane of the general formula (6):

$$R_n R'_h Si_2 Cl_{6-n-h} \tag{6}$$

wherein R, R' and n are as defined above, h is an integer of at least 1, $h \leq 6-n$.

EXAMPLE

Examples of the invention are given below by way of illustration and not by way of limitation.

EXAMPLE 1

A pressure resistant reactor equipped with a stirrer, thermometer, gas feed tube, and distillation tube was charged with 27.0 g (1 mol) of aluminum powder. The reactor was fully dried by heating to 130° C. while passing nitrogen therethrough. Then dry hydrogen chloride gas was passed through the reactor which was heated to 160° C. The reactor was charged with 193.5 g of dimethyldichlorosilane and 2.0 g of ethyl bromide. A valve to the distillation tube was closed. While the reactor was controlled to a reaction temperature of 50° C., 52.0 g of methyl chloride gas was fed to the reactor. The reaction completed in 15 hours. After the residual methyl chloride was purged off, the liquid contents were distilled, obtaining trimethylchlorosilane in a yield of 79.2%.

EXAMPLE 2

The procedure of Example 1 was repeated except that 66.0 g of ethyl chloride gas was fed instead of the methyl chloride gas. The reaction completed in 7 hours. After the residual ethyl chloride was purged off, the liquid contents were distilled, obtaining ethyldimethylchlorosilane in a yield of 62.1% and diethyldimethylsilane in a yield of 12.9%.

EXAMPLE 3

The procedure of Example 1 was repeated except that 149.5 g of methyltrichlorosilane was used instead of 193.5 g of dimethyldichlorosilane and the reaction temperature was 160° C. The reaction completed in 27 hours. After the residual methyl chloride was purged off, the liquid contents were distilled, obtaining trimethylchlorosilane in a yield of 62.1%.

EXAMPLE 4

The procedure of Example 3 was repeated except that 7.5 g of trimethylchlorosilane was added when methyltrichlorosilane and ethyl bromide were admitted and the reaction temperature was 80° C. The reaction completed in 11 hours. After the residual methyl chloride was purged off, the liquid contents were distilled, obtaining trimethylchlorosilane in a yield of 78.1%.

EXAMPLE 5

An autoclave equipped with a stirrer, thermometer and a gas inlet tube was charged with a mixture of 27.0 g of metallic aluminum and 2.0 g of aluminum chloride. While passing dry hydrogen chloride gas, the autoclave was heated to 100° C. The autoclave was charged with 93.3 g of a liquid consisting of up to 50% by weight of 1,1,2,2-tetrachloro-1,2-dimethyldisilane, up to 47% by weight of 1,2,2-trichloro-1,1,2-trimethyldisilane, and up to 3% by weight of an unidentified matter as analyzed by gas chromatography and 2.0 g ethyl bromide. While the autoclave was controlled to a reaction temperature of 150° C., 83.3 g of methyl chloride gas was fed over 15 hours. After the residual methyl chloride gas was purged off, the liquid contents were subject to fractional distillation, obtaining hexamethyldisilane if a yield of 53.11% and chloropentamethyldisilane in a yield of 11.2%.

EXAMPLE 6

The procedure of Example 5 was repeated except that 7.0 g of dimethyldichlorosilane was added when the chlorodisilanes and ethyl bromide were admitted. Reaction at 80° C. for 10 hours gave hexamethyldisilane in a yield of 83.2% and chloropentamethyldisilane in a yield of 12.1%.

EXAMPLE 7

The procedure of Example 5 was repeated except that 7.0 g of tetramethylsilane was added when the chlorodisilanes and ethyl bromide were admitted. Reaction at 50° C. for 10 hours gave hexamethyldisilane in a yield of 83.7% and chloropentamethyldisilane in a yield of 10.7%.

EXAMPLE 8

The procedure of Example 5 was repeated except that 7.0 g hexamethyldisilane was added when the chlorodisilanes and ethyl bromide were admitted. Reaction at 50° C. for 10 hours gave hexamethyldisilane in a yield of 84.1% and chloropentamethyldisilane in a yield of 11.2%.

EXAMPLE 9

A 500-ml autoclave equipped with a stirrer, thermometer and a gas inlet tube was charged with 36.2 g of a liquid consisting of up to 50% by weight of 1,1,2,2-tetrachloro-1,2-dimethyldisilane and up to 47% by weight of 1,2,2-trichloro-1,1,2-trimethyldisilane as analyzed by gas chromatography, 75.0 g of tetramethylsilane, 2.0 g of methyldichlorosilane, and 2.0 g of dry aluminum chloride powder. The contents were agitated at 80° C. for about 3 hours. Then the reaction system was cooled and the residual pressure was released to atmospheric pressure. 2.0 g of ethyl bromide and 21.0 g of metallic aluminum powder were added to the autoclave which was adjusted to 50° C. 110 g of methyl chloride was fed over 10 hours. The reaction solution was filtered and the filtrate was distilled, obtaining 45.4 g (yield 89%) of hexamethyldisilane.

EXAMPLE 10

The procedure of Example 9 was repeated except that 256 g of hexamethyldisilane was used instead of 75.0 g of tetramethylsilane, obtaining 93.9 g (yield 95%) of hexamethyldisilane.

According to the present invention, silanes having a high degree of hydrocarbon substitution can be easily synthesized from chloromonosilanes or chlorodisilanes under moderate conditions and with high volumetric efficiency. The method is economical since the reagents used are aluminum or aluminum alloys and halogenated hydrocarbons which are inexpensive and readily available.

Japanese Patent Application Nos. 5-345212, 6-040500 and 6-148660 are incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. A method for introducing a hydrocarbon into a chlorosilane, comprising the step of reacting a chlorosilane of the general formula (1) or (2):

$$R_m SiCl_{4-m} \quad (1)$$

$$R_n Si_2 Cl_{6-n} \quad (2)$$

wherein R is a hydrogen atom or monovalent hydrocarbon group, a plurality of R groups may be identical or different, letter m is an integer of 0 to 3, and n is an integer of 0 to 5, with a halogenated hydrocarbon of the general formula (3):

$$R'X \quad (3)$$

wherein R' is a monovalent hydrocarbon group and X is a halogen atom, in a liquid phase at a temperature of 20° to 150° C. in the presence of metallic aluminum or an aluminum alloy, thereby substituting the hydrocarbon group R' for at least one chlorine atom of the chlorosilane.

2. The method for introducing a hydrocarbon into a chlorosilane according to claim 1, wherein a chlorosilane of the general formula (1A) or (2A):

$$R_x SiCl_{4-x} \quad (1A)$$

$$R_y Si_2 Cl_{6-y} \quad (2A)$$

wherein R is as defined above, x is an integer of 0 to 2, and y is an integer of 0 to 4, is reacted with a halogenated hydrocarbon of formula (3) in the presence of a silane of the general formula (4):

$$R'_b Si_a Cl_{2a+2-b} \quad (4)$$

wherein R' is a monovalent hydrocarbon group, letter a is an integer of at least 1 and b is equal to 2a, 2a+1 or 2a+2.

3. The method for introducing a hydrocarbon into a chlorosilane according to claim 1, wherein R in formula (1) or (2) represents a saturated or unsaturated monovalent hydrocarbon group having 1 to 20 carbon atoms.

4. The method for introducing a hydrocarbon into a chlorosilane according to claim 1, wherein n in formula (2) is an integer of 2 to 5.

5. The method for introducing a hydrocarbon into a chlorosilane according to claim 1, wherein the chlorosilane represented by formula (1) is selected from the group consisting of tetrachlorosilane, methyltrichlorosilane, methylhydrogendichlorosilane, dimethyldichlorosilane, dimethylhydrogenchlorosilane, ethyltrichlorosilane and isopropyltrichlorosilane.

6. The method for introducing a hydrocarbon into a chlorosilane according to claim 1, wherein the chlorosilane represented by formula (2) is selected from the group consisting of 1,1,2,2-tetrachloro-1,2-dimethyldisilane, 1,1,1,2-tetrachloro-2,2-dimethyldisilane, 1,1,2-trichloro-1,2,2-trimethyldisilane, 1,2-dichloro-1,1,2,2-tetramethyldisilane, 1,1-dichloro-1,2,2,2-tetramethyldisilane, 1-chloro-1,1,2,2,2-pentamethyldisilane and 1,1-dichloro-1,2,2,2-tetraethyldisilane.

7. The method for introducing a hydrocarbon into a chlorosilane according to claim 1, wherein R' in formula (3) is a monovalent hydrocarbon group having 1 to 10 carbon atoms.

8. The method for introducing a hydrocarbon into a chlorosilane according to claim 1, wherein X in formula (3) is chlorine, fluorine, bromine or iodine.

9. The method for introducing a hydrocarbon into a chlorosilane according to claim 1, wherein the halogenated hydrocarbon is selected from the group consisting of methyl chloride, ethyl chloride, t-butyl chloride, cyclohexyl chloride, methyl iodide and ethyl bromide.

10. The method for introducing a hydrocarbon into a chlorosilane according to claim 1, wherein 1 to 1.5 mole of the halogenated hydrocarbon is reacted per mole Si—Cl bond in the chlorosilane represented by formula (1) or (2).

11. The method for introducing a hydrocarbon into a chlorosilane according to claim 1, wherein the metallic aluminum or aluminum alloy is selected from the group consisting of Al, AlMgSi and AlCuMgo.

12. The method for introducing a hydrocarbon into a chlorosilane according to claim 1, wherein 0.6 to 2.7 mole metallic aluminum or aluminum alloy is used per mole Si—Cl bond in the chlorosilane represented by formula (1) or (2).

13. The method for introducing a hydrocarbon into a chlorosilane according to claim 2, wherein the silane represented by formula (4) is selected from the group consisting of (4A), (4B) and 4(C)

$$R'_{2a} Si_a Cl_2 \quad (4A)$$

$$R'_{2a+1} Si_a Cl \quad (4B)$$

$$R'_{2a+2} Si_a \quad (4C).$$

14. The method for introducing a hydrocarbon into a chlorosilane according to claim 2, wherein the silane represented by formula (4) is selected from the group consisting of dichlorodimethylsilane, chlorotrimethylsilane, tetramethylsilane, 1-chloro-1,1,2,2,2-pentamethyldisilane, hexamethyldisilane, 1-chloroheptamethyltrisilane, octamethyltrisilane, decamethyltetrasilane, tetraethylsilane, hexaethyldisilane and octaethyltrisilane.

15. The method for introducing a hydrocarbon into a chlorosilane according to claim 2, wherein the silane represented by formula (4) is selected from the group consisting of tetramethylsilane, hexamethyldisilane, octamethyltrisilane, decamethyltetrasilane, tetraethylsilane, hexaethyldisilane and octaethyltrisilane.

16. The method for introducing a hydrocarbon into a chlorosilane according to claim 2, wherein 1 to 20 mole % of the silane represented by formula (4) is used based on the moles of the chlorosilane represented by formula (1) or (2).

17. The method for introducing hydrocarbon into a chlorosilane according to claim 1, wherein the chlorosilane is reacted with the halogenated hydrocarbon in a liquid phase in the presence of a metallic aluminum or an aluminum alloy at a temperature of 20° to 150° C. and a pressure of 0 to 10 kgw/cm$^2$G for 5 to 20 hours.

18. The method for introducing a hydrocarbon into a chlorosilane according to claim 2, further comprising a redistribution reaction between the chlorosilane represented by formula (1) or (2) and the silane represented by formula (4) in the presence of a Lewis acid catalyst selected from the group consisting of aluminum chloride, aluminum bromide, boron trichloride and ferric chloride.

19. The method for introducing a hydrocarbon into a chlorosilane according to claim 18, wherein 0.5 to 10% by weight of the Lewis acid catalyst is used based on the weight of chlorosilane represented by formula (1) or (2).

20. The method for introducing a hydrocarbon into a chlorosilane according to claim 18, wherein the redistribution reaction is carried out at a temperature of 20° to 150° C. and a pressure of 0 to 10 kg/cm$^2$G for ½ to 5 hours.

21. The method for introducing a hydrocarbon into a chlorosilane according to claim 2, wherein 1 to 1.5 mole of the halogenated hydrocarbon is reacted per mole Si—Cl bond in the chlorosilane represented by formula (1) or (2).

* * * * *